US00PP16913P2

(12) United States Plant Patent
Durio

(10) Patent No.: US PP16,913 P2
(45) Date of Patent: Aug. 1, 2006

(54) ***CARYOPTERIS* PLANT NAMED 'DURIO'**

(50) Latin Name: *Caryopteris×clandonensis*
Varietal Denomination: Durio

(75) Inventor: Dalton E. Durio, Opelousas, LA (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 3 days.

(21) Appl. No.: 11/077,418

(22) Filed: Mar. 10, 2005

(51) Int. Cl.
*A01H 5/00* (2006.01)

(52) U.S. Cl. ..... Plt./226

(58) Field of Classification Search ..... Plt./226, Plt./263

See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Caryopteris* plant named 'Durio', characterized by its upright, outwardly spreading and mounded plant habit; freely branching growth habit; relatively large leaves; and numerous large pink-colored flowers.

1 Drawing Sheet

Botanical designation: *Caryopteris×clandonensis* cultivar Durio.

BACKGROUND OF THE INVENTION

The present Invention relates to a new and distinct cultivar of *Caryopteris* plant, botanically known as *Caryopteris×clandonensis*, and hereinafter referred to by the name 'Durio'.

The new cultivar is a chance seedling that originated from a self-pollination in 1998 of the *Caryopteris×clandonensis* cultivar Blue Mist, not patented. The cultivar Durio was discovered and selected by the Inventor in 1998 as a single flowering plant within the progeny of the stated self-pollination in a controlled environment in Opelousas, La.

Asexual reproduction of the new cultivar by softwood cuttings in Opelousas, La. since 1999, has shown that the unique features of this new *Caryopteris* are stable and reproduced true to type in successive generations of asexual reproduction.

SUMMARY OF THE INVENTION

The following traits have been repeatedly observed and are determined to be the unique characteristics of 'Durio'. These characteristics in combination distinguish 'Durio' as a new and distinct cultivar:

1. Upright, outwardly spreading and mounded plant habit.
2. Freely branching growth habit.
3. Relatively large leaves.
4. Numerous large pink-colored flowers.

In side-by-side comparisons conducted in Grand Haven, Mich., plants of the new *Caryopteris* differed primarily from plants of the parent, the cultivar Blue Mist in flower color as plants of the cultivar Blue Mist had violet blue-colored flowers. In addition, plants of the new *Caryopteris* had broader leaves and larger flowers than plants of the cultivar Blue Mist.

The new *Caryopteris* can also be compared to the *Caryopteris* cultivar, Jason, disclosed in U.S. Plant patent application Ser. No. 10/878,606. In side-by-side comparisons conducted in Grand Haven, Mich., plants of the new *Caryopteris* differed from plants of the cultivar Jason in the following characteristics:

1. Plants of the new *Caryopteris* were more compact than plants of the cultivar Jason.
2. Plants of the new *Caryopteris* had larger leaves with longer petioles than plants of the cultivar Jason.
3. Plants of the new *Caryopteris* and the cultivar Jason differed in leaf and flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet is a close-up view of typical flowers and leaves of 'Durio'.

The photograph at the bottom of the sheet comprises a side perspective view of a typical plant of 'Durio' grown in an outdoor nursery. Flower and foliage colors in the photographs may differ slightly from the color values cited in the detailed botanical description which accurately describe the colors of the new *Caryopteris*.

DETAILED BOTANICAL DESCRIPTION

The cultivar Durio has not been observed under all possible environmental conditions. The phenotype may vary somewhat with variations in environment such as temperature and light intensity, without, however, any variance in genotype. The aforementioned photograph and following obervations and measurements describe plants grown in Grand Haven, Mich., under commercial practice in an outdoor nursery during the summer and fall. Plants used for the photograph and description were about 2.5 years old. In the following description, color references are made to The Royal Horticultural Society Colour Chart, 1995 Edition, except where general terms of ordinary dictionary significance are used.

Botanical classification: *Caryopteris×clandonensis* cultivar Durio.

Parentage: Self-pollination of *Caryopteris×clandonensis* cultivar Blue Mist, not patented.

Propagation:

*Type cutting.*—Softwood cuttings.

*Time to initiate roots.*—About 10 days at 20° C.

*Time to develop roots.*—About two months at 20° C.

*Root description.*—Fine; freely branching; white in color.

Plant description:

*General appearance.*—Deciduous shrub. Upright, outwardly spreading and mounded plant habit.

*Growth and branching habit.*—Freely branching; about 67 lateral branches develop per plant. Pinching, that is, removal of the terminal apices, enhances branching with lateral branches potentially forming at every node. Strong and vigorous growth habit.

*Plant height.*—About 30 cm.

*Plant diameter or spread.*—About 40 cm.

*Lateral branch description.*—Length: About 31 cm. Diameter: About 4 mm. Internode length: About 4.2 cm. Texture: Pubescent. Strength: Moderately strong. Color: Young stems, 186A; older stems, 146B.

*Foliage description.*—Arrangement: Opposite, simple. Length: About 6.5 cm. Width: About 3.8 cm. Shape: Ovate. Apex: Broadly acute. Base: Obtuse to truncate. Margin: Crenate to dentate. Texture, upper and lower surfaces: Pubescent. Venation pattern: Pinnate. Color: Developing foliage, upper surface: 139A. Developing foliage, lower surface: 138B. Fully expanded foliage, upper surface: 137A; venation, 137A. Fully expanded foliage, lower surface: 138B; venation, 138D. Petiole: Length: About 1.5 cm. Diameter: About 2 mm. Texture, upper and lower surfaces: Pubescent. Color, upper and lower surfaces: 138D.

Flower description:

*Flower type and habit.*—Small single flowers arranged on axillary cymes. Very freely flowering with about 45 flowers and flower buds per inflorescence; about 630 flowers and flower buds per lateral branch. Flowers last about six to eight weeks on the plant. Flowers not persistent. Flowers not fragrant.

*Flowering season.*—In the garden, flowering is continuous during September and October in Grand Haven, Mich.

*Inflorescence height.*—About 26 cm.

*Inflorescence diameter.*—About 4 cm.

*Flower diameter.*—About 9 mm.

*Flower depth.*—About 9 mm.

*Flower buds.*—Length: About 3 mm. Diameter: About 2 mm. Shape: Ovate to elliptic. Color: 139C.

*Petals.*—Quantity/arrangement: Five per flower fused at base; one petal larger than the other four petals. Petal length: Four smaller petals, about 2 mm; larger petal, about 3 mm. Petal width: Four smaller petals, about 1 mm; larger petal, about 1 mm. Shape: Four smaller petals, broad lobes; larger petal, lanceolate. Apex, all petals: Acute. Margin: Four smaller petals, entire; larger petal, fringed. Texture, upper and lower surfaces: Glabrous, smooth. Color: When opening, upper surface: 62C. When opening, lower surface: 62B. Fully opened, upper and lower surfaces: 62C; color fading to 62D with development.

*Sepals.*—Quantity/arrangement: Five, fused; campanulate. Calyx length: About 5 mm. Calyx diameter: About 3 mm. Sepal length: About 5 mm. Sepal width: About 1 mm. Shape: Lanceolate. Apex: Acute. Margin: Entire. Texture, upper and lower surfaces: Slightly pubescent. Color: Immature, upper and lower surfaces: 191B. Mature, upper and lower surfaces: 143C.

*Peduncles.*—Length: About 3 mm. Diameter: About 0.75 mm. Texture: Pubescent. Strength: Strong. Angle to stem: About 30° from vertical. Color: 191B.

*Pedicels.*—Length: About 5 mm. Diameter: About 1.5 mm. Texture: Pubescent. Strength: Strong. Angle to stem: About 10° from vertical. Color: 191B.

*Reproductive organs.*—Stamens: Quantity: Four per flower. Anther shape: Oval. Anther length: About 0.5 mm. Anther color: 177D. Pollen amount: Scarce. Pollen color: 177D. Pistils: Quantity: One per flower. Pistil length: About 1.2 cm. Stigma shape: Bi-parted. Stigma color: 177D. Style length: About 9 mm. Style color: 65D. Ovary color: Close to 145A.

*Seed/fruit.*—Seed and fruit development have not been observed.

Disease/pest resistance: Plants of the new *Caryopteris* have not been observed to be resistant to pathogens and pests common to *Caryopteris.*

Temperture tolerance: Plants of the new *Caryopteris* have been observed to tolerate temperatures from −25 to 38° C.

It is claimed:

1. A new and distinct cultivar of *Caryopteris* plant named 'Durio', as illustrated and described.

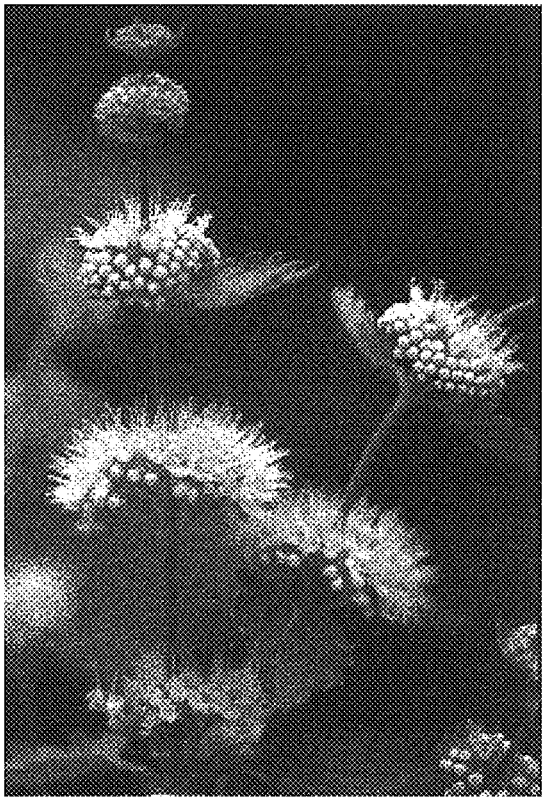
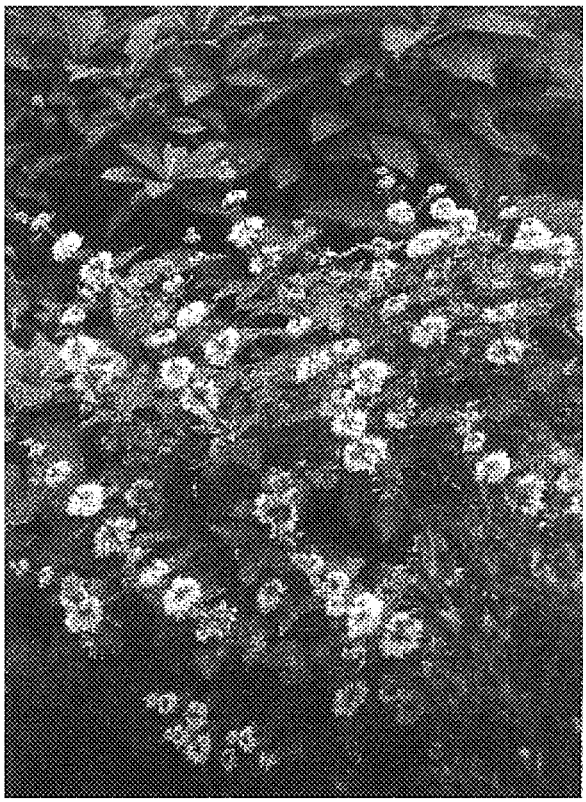

* * * * *